United States Patent [19]

Blade

[11] Patent Number: 4,713,200

[45] Date of Patent: Dec. 15, 1987

[54] PESTICIDAL COMPOUNDS

[75] Inventor: Robert J. Blade, Berkhamsted, England

[73] Assignee: Burroughs Wellcome Co., Research Triangle Park, N.C.

[21] Appl. No.: 717,449

[22] Filed: Mar. 29, 1985

[30] Foreign Application Priority Data

| Apr. 3, 1984 | [GB] | United Kingdom | 8408566 |
| Apr. 11, 1984 | [GB] | United Kingdom | 8409361 |
| Aug. 15, 1984 | [GB] | United Kingdom | 8420753 |
| Nov. 21, 1984 | [GB] | United Kingdom | 8429372 |

[51] Int. Cl.$^4$ ............................. C11C 1/00; C11C 3/00
[52] U.S. Cl. ....................................... 260/408; 260/413
[58] Field of Search ........... 260/413 R, 413 K, 413 L, 260/413 Q, 413 M, 408; 562/405, 426, 429, 431, 465, 466, 469, 471, 472, 490

[56] References Cited

U.S. PATENT DOCUMENTS

| 2,484,295 | 10/1949 | Kilgore | 167/30 |
| 2,500,582 | 3/1950 | Smith et al. | 260/599 |
| 2,629,741 | 2/1953 | Drake | 260/600 |
| 3,755,411 | 8/1973 | Henrick et al. | 260/465.6 |
| 3,865,852 | 2/1975 | Henrick et al. | 260/402.5 |
| 4,069,344 | 1/1978 | Karrer | 424/324 |

FOREIGN PATENT DOCUMENTS

| 57-212150 | 12/1982 | Japan. |
| 2027702 | 2/1980 | United Kingdom. |
| 2101600 | 1/1983 | United Kingdom. |

OTHER PUBLICATIONS

Rapoport et al, *Journal of the American Chemical Society*, 69, 471–472 (1947).

Schmidt et al, *Synthesis*, vol. 11, pp. 893–996 (1982).

*Primary Examiner*—Charles F. Warren
*Assistant Examiner*—Elizabeth A. Hanley
*Attorney, Agent, or Firm*—Donald Brown

[57] ABSTRACT

Pesticidal compounds, their production, formulation into pesticidal compositions and use against pests, particularly insects and acarines.

1 Claim, No Drawings

PESTICIDAL COMPOUNDS

This invention relates to pesticidal compounds, their production, formulation into pesticidal compositions and use against pests, particularly insects and acarines.

The present invention provides compounds of Formula (I):

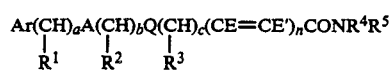  (I)

wherein: Ar is

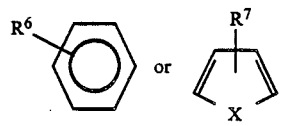

or naphthyl (optionally substituted by $R^6$) $R^6$ being one or more of hydrogen, halo, alkyl, alkenyl, alkynyl, alkoxy, amino, alkenoxy, acyloxy, acyl, all being optionally substituted, methylenedioxy, cyano, nitro, $SOR^8$, $SO_2R^8$, $SR^9$, $SO_2NR^{10}R^{11}$, aryl, aryloxy or $CO_2R^{12}$ where $R^8$ to $R^{12}$ are all independently alkyl, $R^7$ being halo, or optionally substituted alkyl and X being oxygen, sulphur, NH or N-alkyl;

A is —O—, —N($R^{13}$)— (where $R^{13}$ is hydrogen, alkyl or acyl), $S(O)_d$ where d is 0, 1 or 2, or a carbonyl group; a is 0 to 3; b is 0 to 12; each $R^1$ is independently hydrogen, alkyl, fluoro, cyano or alkynyl and each of $R^2$ and $R^3$ are each chosen independently from hydrogen, alkyl and halo; Q is —$CH_2$— or oxygen; c is 0 to 12; n is 0, 1 or 2; each E and E' is independently hydrogen or halo; and $R^4$ and $R^5$ are each independently hydrogen, alkyl, cycloalkyl, alkenyl or alkoxy (any of which are optionally substituted by halo, alkenyl, alkyl, cycloalkyl, alkoxy, alkynyl or cyano), or $NR^4R^5$ forms a 5, 6 or 7 membered heterocyclic group; provided that a is 0 only where Q is an oxygen.

A particularly preferred series of compounds are those of Formula (IA):

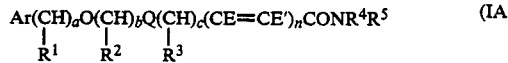  (IA)

wherein the substituents are as defined above.

Preferably the sum of b and c is no more than 12, most preferably 3 to 7. When Q is a methylene group, the sum of b and c is preferably an odd number, most preferably 3 or 5. If either of $R^6$ and $R^7$ are substituted alkyl, then it is preferred that the group be trifluoromethyl. "Alkyl", "alkenyl" and similar groups referred to above preferably have from 1 to 6 carbon atoms. When either $R^4$ or $R^5$ is an alkenyl group, it is preferably saturated in the α-position. "Aryl" and "aryloxy" include phenyl and substituted phenyl. The optional substituents for when $R^6$ is alkyl and for when $R^7$ is alkyl etc include alkyl, halo, aryl (preferably phenyl), nitro, alkenyl, alkynyl, alkoxy, acyl.

Suitably, $R^4$ is a branched alkyl group such as isobutyl, and $R^5$ is hydrogen. It has been found that acaricidal activity is enhanced if there is an alkyl group α to the nitrogen whereas insecticidal activity is enhanced by other configurations. Conveniently, the configuration of the or each olefinic group conjugated to the carbonyl group is E.

$R^6$ is preferably an electron-withdrawing group such as halo or trifluoromethyl. Ar is preferably a phenyl group, and $R^6$ is then preferably one or two trifluoromethyl groups. When there is only one $CF_3$ group, this is preferably at the meta position.

E is preferably hydrogen and, most preferably, E and E' are both hydrogen. If either is not hydrogen, however, then the preferred halo entity is fluoro.

Compounds of Formula (I) may be prepared in any of the following ways:

(a) by amidation of the corresponding acid or acid derivative, ie. by reaction of a compound of Formula (II) with a compound of Formula (III):

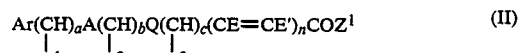  (II)

  (III)

wherein $Z^1$ is hydroxyl, halo or a phosphoroimidate ester group

and the other variables are as defined above.

(b) by reaction of a compound of Formula (IV) with a compound of Formula (V) or (VI):

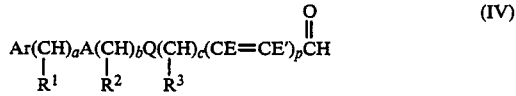  (IV)

  (V)

  (VI)

wherein $Z^2$ is alkyl, alkoxy (preferably ethoxy) or aryl (preferably phenyl), and $p + q = n - 1$.

(c) by reaction of a compound of Formula (VII) with a compound of Formula (VIII):

  (VII)

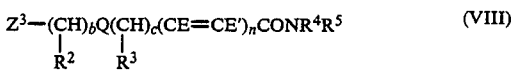  (VIII)

where $Z^3$ is —OH or a suitable leaving group such as halo; the positions of —AH and $Z^3$— with respect to the two compounds may be exchanged to create the —A— linkage in an exactly analogous reaction.

(d) when Q is oxygen, by reaction of a compound of Formula (IX) with a compound of Formula (X):

  (IX)

-continued

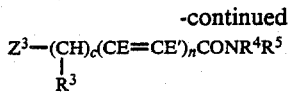 (X)

again, the positions of the —OH and $Z^3$— may be reversed between the respective compounds, to give an analogous reaction.

(e) by reaction of a compound of Formula (XI) with a compound of Formula (XII):

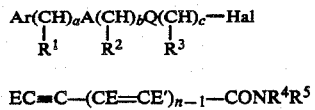 (XI)

$$EC\equiv C-(CE=CE')_{n-1}-CONR^4R^5 \quad (XII)$$

where Hal is a halogen atom; or (f) by an elimination reaction involving a compound of Formula (XIII):

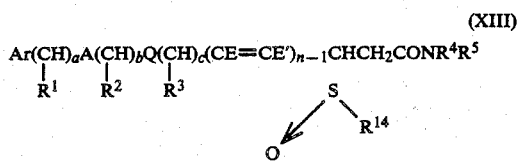 (XIII)

where $R^{14}$ is a suitable group, such as lower alkyl.

(g) by reacting a compound of Formula (XIV) with a compound of Formula (XV):

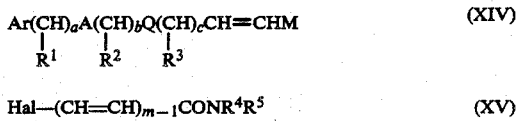 (XIV)

$$Hal-(CH=CH)_{m-1}CONR^4R^5 \quad (XV)$$

wherein Hal is halide, for example bromo or iodo, and M is a metal atom for example zinc, zirconium or aluminium or a metal-containing group, such as a bis-(cyclopentadienyl)zirconium chloride group.

Process (a) is normally carried out in an aprotic solvent, such as ether, dichloromethane or benzene, optionally in the presence of a tertiary amine, such as triethylamine, but in the absence of water, at room temperature or below.

Process (b) is carried out in an anhydrous inert solvent, for example an ether such as tetrahydrofuran, optionally in the presence of a base, and preferably in the absence of oxygen, e.g. under a nitrogen atmosphere, at a low temperature ($-40°$ to $0°$ C.). The Wittig-type reagent may be obtained with lithium diisopropylamide.

When processes (c) and (d) comprise the reaction of two alcohols, this is preferably in the presence of a dehydrating agent, such as concentrated sulphuric acid, in a non-polar solvent at about $80°-110°$ C. When $Z'''$ is halo, a base is preferably present. Other standard methods for the formation of ethers and thioethers, such as those described in "Compendium of Organic Synthetic Methods", Harrison and Harrison, Wiley Interscience, (New York) 1971, may be used.

Process (f) may be effected by refluxing in a suitable non-polar solvent, such as benzene, toluene or xylene. The compound of Formula (XIII) may be prepared by oxidation, for example with periodate, of the corresponding compound having an —$SR^{14}$ group. This latter compound, in turn, may be prepared by reaction of a compound of Formula (XVI) with a compound of Formula (XVII):

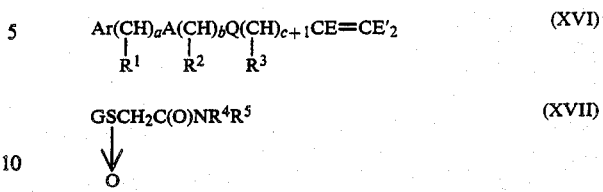

Where G is an alkyl or aryl group preferably, the compound of Formula (XVII) is reacted with trifluoroacetic anhydride in trifluoro acetic acid and then the compound of Formula (XVI) is added, at $0°-20°$ C.

The intermediates of Formulae (II)–(XVII) may be prepared by standard methods. For example, the compounds of Formulae (V) and (VI) may be prepared by the reaction of an appropriate phosphine, phosphonate or phosphite with an w-halo amide. Compounds of Formula (IV) may be prepared by hydrolysis of a ketal ring or oxidation of an alcohol.

The carbonyl-containing compounds (IV) may be prepared by oxidation of the corresponding alcohol, for example using pyridinium chlorochromate or oxalyl chloride/DMSO. The acid function in Formula (II) may be prepared by hydrolysis of an ester, the ester being prepared by a conventional Wittig or Wadsworth-Emmons reaction, using eg. an aldehyde and ethoxycarbonylmethylene triphenylphosphorane or the anion from triethylphosphonocrotonate. The acid function in Formula (II) may alternatively be prepared by hydrolysis of esters of Formula (XVIII):

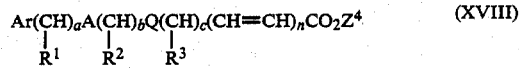 (XVIII)

Compounds (XVIII) can be prepared by elimination on a compound of Formula (XIX):

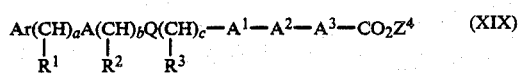 (XIX)

wherein $Z^4$ is as defined above, one of $A^1$, $A^2$ and $A^3$ is $(CH=CH)_{m-1}$, another of $A^1$, $A^2$ and $A^3$ is —$CH_2$—, the third of $A^1$, $A^2$ and $A^3$ is —$CH(OZ^5)$, $Z^5$ being H or acyl such as acetyl, and the said —$CH_2$— and —CH-$(OZ^5)$—, $Z^5$ being H or acyl such as acetyl, and the said —$CH_2$— and —$CH(OZ^5)$— groups are adjacent one another. The reaction is preferably carried out in an aromatic solvent, conveniently in the presence of a molybdenum catalyst (e.g. molydenum hexacarbonyl) and a base, such as bis-trimethylsilylacetamide.

Intermediates of Formula (XIX) may be obtained by reaction of a suitable aldehyde with a suitable sulphinyl compound, followed by acylation.

The reaction is carried out in a suitable solvent such as acetonitrile with a base such as piperidine. The alcohols from which compounds (IV) and (VII) are prepared may be synthesised by the reaction of a compound of Formula (XX) with a compound of Formula (XXI):

 (XX)

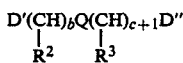 (XXI)

Where each D,D' and D" is independently hydroxyl or halo and D" may alternatively be a protected hydroxyl group.

Process (g) is normally carried out in, for example, vinyl-bis-(cyclopentadienyl)zirconium chloride in tetrahydrofuran in the presence of a palladium (O) catalyst.

When D" is halo then compounds of Formula (XXI) may be prepared by the reaction of a compound of Formula (XXII) with a compound of Formula (XXIII):

 (XXII)

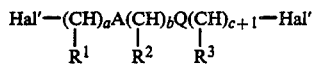 (XXIII)

wherein M' is a metal atom, preferably lithium, and each Hal' is independently halo, preferably chloro. The reaction proceeds in a suitable inert solvent, for example an ether such as tetrahydrofuran.

Compounds (XXII) may be prepared from the aryl halide (preferably iodo or bromo).

The compounds of Formula (I) may be used to control arthropods such as insect and acarine pests.

The compounds of Formula (I) may be used for such purposes by application of the compounds themselves or in diluted form in known fashion as a dip, spray, lacquer, foam, dust, powder, aqueous suspension, paste, gel, shampoo, grease, combustible solid, vapourising mat, wettable powder, granule, aerosol, emulsifiable concentrate, oil suspensions, oil solutions, pressure-pack, impregnated article or pour on formulation. Dip concentrates are not applied per se, but diluted with water and the animals immersed in a dipping bath containing the dip wash. Sprays may be applied by hand or by means of a spray race or arch. The animal may be saturated with the spray by means of high volume application or superficially coated with the spray by means of light or ultra low volume application. Aqueous suspensions may be applied to the animal in the same manner as sprays or dips. Dusts may be distributed over the animals by means of a powder applicator or incorporated in perforated bags attached to trees or rubbing bars. Pastes, shampoos and greases may be applied manually or distributed over the surface of an inert material against which animals rub and transfer the material to their skins. Pour-on formulations are dispensed as a unit of liquid of small volume on to the backs of animals such that all or most of the liquid is retained on the animals.

The compounds of Formula (I) or acid addition salts thereof may be formulated either as formulations ready for use on the animals or as formulations requiring dilution prior to application, but both types of formulation comprise a compound of Formula (I) in intimate admixture with one or more carriers or diluents. The carriers may be liquid, solid or gaseous or comprise mixtures of such substances, and the compound of Formula (I) may be present in a concentration of from 0.025 to 99% w/v depending upon whether the formulation requires further dilution.

Dusts, powder and granules comprise the compound of Formula (I) in intimate admixture with a powdered solid inert carrier for example suitable clays, kaolin, talc, mica, chalk, gypsum, vegetable carriers, starch and diatomaceous earths.

Sprays of a compound of Formula (I) may comprise a solution in an organic solvent (e.g. those listed below) or an emulsion in water (dip wash or spray wash) prepared in the field from an emulsifiable concentrate (otherwise known as a water miscible oil) which may also be used for dipping purposes. The concentrate preferably comprises a mixture of the active ingredient, with or without an organic solvent and one or more emulsifiers. Solvents may be present within wide limits but preferably in an amount of from 0 to 90% w/v of the composition and may be selected from kerosene, ketones, alcohols, xylene, aromatic naphtha, and other solvents known in the formulating art. The concentration of emulsifiers may be varied within wide limits but is preferably in the range of 5 to 25% w/v and the emulsifiers are conveniently non-ionic surface active agents including polyoxyalkylene esters of alkyl phenols and polyoxyethylene derivatives of hexitol anhydrides and anionic surface active agents including Na lauryl sulphate, fatty alcohol ether sulphates, Na and Ca salts of alkyl aryl sulphonates and alkyl sulphosuccinates.

Wettable powders comprise an inert solid carrier, one or more surface active agents, and optionally stabilisers and/or anti-oxidants.

Emulsifiable concentrates comprise emulsifying agents, and often an organic solvent, such as kerosene, ketones, alcohols, xylenes, aromatic naphtha, and other solvents known in the art.

Wettable powders and emulsifiable concentrates will normally contain from 5 to 95% by weight of the active ingredient, and are diluted, for example with water, before use.

Lacquers comprise a solution of the active ingredient in an organic solvent, together with a resin, and optionally a plasticiser.

Dip washes may be prepared not only from emulsifiable concentrates but also from wettable powders, soap based dips and aqueous suspensions comprising a compound of Formula (I) in intimate admixture with a dispersing agent and one or more surface active agents.

Aqueous suspensions of a compound of Formula (I) may comprise a suspension in water together with suspending, stabilizing or other agents. Aqueous solutions may also be formed from acid addition salts of a compound of the Formula (I). The suspensions or solutions may be applied per se or in a diluted form in known fashion.

Greases (or ointments) may be prepared from vegetable oils, synthetic esters of fatty acids or wool fat together with an inert base such as soft paraffin. A compound of Formula (I) is preferably distributed uniformly through the mixture in solution or suspension. Greases may also be made from emulsifiable concentrates by diluting then with an ointment base.

Pastes and shampoos are also semi-solid preparations in which a compound of Formula (I) may be present as an uniform dispersion in a suitable base such as soft or liquid paraffin or made on a non-greasy basis with glycerin, mucilage or a suitable soap. As greases, shampoos and pastes are usually applied without further dilution they should contain the appropriate percentage of the compound of Formula (I) required for treatment.

Aerosol sprays may be prepared as a simple solution of the active ingredient in the aerosol propellant and co-solvent such as halogenated alkanes and the solvents referred to above, respectively. Pour-on formulations may be made as a solution or suspension of a compound of Formula (I) in a liquid medium which also contains a viscous oil to minimise spreading of the formulation on the surface of the animals. An avian or mammal host may also be protected against infestation of acarine ectoparasites by means of carrying a suitably-moulded, shaped plastics article impregnated with a compound of Formula (I). Such articles include impregnated collars, tags, bands, sheets and strips suitably attached to appropriate parts of the body.

The concentration of the compound of Formula (I) to be applied to an animal will vary according to the compound chosen, the interval between treatments, the nature of the formulation and the likely infestation, but in general 0.001 to 20.0% w/v and preferably 0.01 to 10% of the compound should be present in the applied formulation. The amount of the compound deposited on an animal will vary according to the method of application, size of the animal, concentration of the compound in the applied formulation, factor by which the formulation is diluted and the nature of the formulation but in general will lie in the range of from 0.0001% to 0.5% except for undiluted formulations such as pour-on formulations which in general will be deposited at a concentration in the range from 0.1 to 20.0% and preferably 0.1 to 10%.

Dusts, greases, pastes and aerosol formulations are usually applied in a random fashion as described above and concentrations of 0.001 to 20% w/v of a compound of Formula (I) in the applied formulation may be used.

Insec pests include members of the orders Coleoptera (e.g. Anobium, Tribolium, Sitophilus, Anthonomus or Anthrenus spp.), Lepidoptera (e.g. Ephestia, Heliothis, Spodoptera or Tineola spp.), Diptera (e.g. Musca, Aedes, Culex, Glossina, Stomoxys, Haematobia, Tabanus, Hydrotaea, Lucilia, Chrysomia, Callitroga, Dermatobia, Hypoderma and Melophagus spp.), Phthiraptera (Malophaga e.g. Damalina spp. and Anoplua e.g. Linognathus and Haematopinus spp.), Hemiptera (e.g. Aphis or Cimex spp.), Orthoptera (e.g. Schistocerca or Acheta spp.), Dictyoptera (e.g. Blattella, Periplaneta or Blatta spp.), Hymenoptera (e.g. Solenopsis or Monomorium spp.), Isoptera (e.g. (Reticulitermes spp.), Siphonaptera (e.g. Ctenocephalides or Pulex spp.), Thysanura (e.g. Lepisma spp.), Dermaptera (e.g. Forficula spp.) and Pscoptera (e.g. Peripsocus spp.).

Acarine pests include ticks, e.g. members of the genera Boophilus, Rhipicephalus, Amblyomma, Hyalomma, Ixodes, Haemaphysalis, Dermocentor and Anocentor, and mites and manges such as Tetranychus, Psoroptes, Psorergates, Chorioptes and Demodex spp.

The compounds exhibit killing and/or knockdown activity against arthropod pests, and can be used to control larval pests as well as adult pests.

Compounds of the invention may be combined with one or more other active ingredients (for example pyrethroids, carbamates and organophosphates) and/or with attractants and the like. Furthermore, it has been found that the activity of the compounds of the invention may be enhanced by the addition of a synergist or potentiator, for example: one of the oxidase inhibitor class of synergists, such as piperonyl butoxide or NIA 16388; a second compound of the invention; or a pyrethroid pesticidal compound. When an oxidase inhibitor synergist is present in a formula of the invention, the ratio of synergist to compound of Formula (I) will be in the range 25:1-1:25 eg about 10:1.

Stabilisers for preventing any chemical degradation which may occur with the compounds of the invention include, for example, antioxidants (such as tocopherols, butylhydroxyanisole and butylhydroxytoluene) and scavengers (such as epichlorhydrin).

It will be understood that what we will claim may comprise:

(a) compounds of Formula (I);
(b) processes for the preparation of compounds of Formula (I);
(c) insecticidal and acaricidal compositions comprising a compound of Formula (I) in admixture with a carrier;
(d) processes for the preparation of such pesticidal compositions;
(e) methods for the control of insect or acarine pests comprising the application to the pest or its environment of a compound of Formula (I);
(f) synergised pesticidal compositions comprising a compound of Formula (I); and
(g) potentiating or non-potentiating mixtures of a compound of Formula (I) and another pesticidal compound;
(h) novel intermediates of the preparation of compounds of Formula (I).

The following examples illustrate, in a non-limiting manner, preferred aspects of the invention.

EXAMPLE 1

N-isobutyl 11-(3'-trifluoromethylbenzyloxy)-(2E,4E)-undecadienamide (a) Sodium metal (0.54 g, 23.3 mmol) was reacted with 1,7-heptanediol (9.3 g, 70.5 mmol) in dry toluene (130 mL) at 100° C. 3-Trifluoromethyl benzyl chloride (5 g, 25.27 mmol) was added at room temperature and the mixture was heated for 1 hour under reflux. The cooled reaction mixture was filtered and the organic phase dried. The crude material obtained upon removal solvent was purified by column chromatography (silica- 1:1, ether:hexane) to give 7.18 g (96% of theory) of 7-(3'-trifluoromethyl-benzyloxy-heptan-1-ol.

(b) Dimethyl sulphoxide (2.13 mL, 27.6 mmol) was added, at −78° C. under nitrogen, to redistilled oxalyl chloride (1.26 mL, 13.8 mmol) in dichloromethane (50 mL). The product of step (a) (4 g, 13.8 mmol) was added at −78° C. After 30 mins at this temperature, triethylamine (9.7 mL) was added and the reaction mixture was allowed to reach room temperature. After washing with water, 2N hydrochloric acid, sodium bicarbonate and brine and then drying and removing the solvent, 7-(3'-trifluoromethylbenzyloxy)-heptan-1-al, 3 g, (76% of theory) was obtained.

(c) Triethyl-4-phosphonocrotonate (2.6 g, 10.45 mmol) in tetrahydrofuran was added at −70° C. and under nitrogen to lithium diisopropylamide (prepared from n-butyl lithium (10 mmol) and diisopropylamine (10.45 mmol)) in dry tetrahydrofuran (7.5 mL). The solution was warmed to 0° C. and re-cooled to −40° C., treated with the product of step (b) (3 g, 10.45 mmol) and left for 18 hours at room temperature. After standard work-up procedures the crude material was purified by column chromatography (silica-30:70 ether:hexane) to give ethyl 11-(3'-trifluoromethylbenzyloxy)-(2E,4E)-undecadienoate, 1.75 g (44% of theory).

(d) The product of step (c) (1.74 g, 4.5 mmol) was hydrolysed with potassium hydroxide (0.88 g) in water (20 mL) and ethanol (60 mL) at room temperature over 18 hours to give 1.0 g (63% of theory) of 11-(3'trifluoromethylbenzyloxy)-(2E,4E)-undecadienoic acid.

(e) The product of step (d) (1 g, 2.8 mmol) was treated with triethylamine (0.66 mL, 4.8 mmol) and phenyl N-phenylphosphoroamidochloridate (1 g, 3.8 mmol) in dry dichloromethane for 30 mins under nitrogen at room temperature. Isobutylamine (0.66 mL, 6.6 mmol) and triethylamine (0.66 mL, 4.8 mmol) were added and after 24 hours the reaction mixture was subjected to standard work-up procedures. The crude product was purified by column chromatography (1:1 hexane:ether, silica) to give 0.57 g (50% of theory) of N-isobutyl 11-(3'trifluoromethylbenzyloxy)-(2E,4E)-undecadienamide. mp 48°-50°.

Nuclear magnetic resonance spectrum (NMR): 7.52, 4H, m, aromatic; 7.2, 1H, d, of m, $J_{3,2}=16$, H3; 6.05, 2H, m, H4,5; 5.78, 1H, d, $J_{2,3}=16$, H2; 5.74, 1H, m, NH; 4.55, 2H, s, benzyl CH$_2$; 3.53, 2H, t, H11; 3.16, 2H, d of d, isobutyl; 2.16, 2H, m, H6; 1.48; 9H, m, isobutyl, H7, 8, 9, 10; 0.93, 6H, d, isobutyl.

Using substantially the same synthetic sequence, but with the diffences noted, the following have been prepared:

EXAMPLE 2

N-isobutyl 9-(3'trifluoromethylbenzyloxy)-(2E,4E)-nonadienamide

In step (a) 1,5-pentanediol was used instead of 1,7-heptanediol.

EXAMPLE 3

N-2-methyl-butyl 9-(3'trifluoromethylbenzyloxy)-(2E-4E)-nonadienamide

In step (a), 1,5 pentanediol was used instead of 1,7-heptanediol and in step (e), 2-methyl-butylamine instead of isobutylamine.

EXAMPLE 4

N-isobutyl 11-(3',5'-bis-trifluoromethylbenzyloxy)-(2E,4E)-undecadienamide

In step (a), 3,5-bis-trifluoromethylbenzyl bromide was used instead of 3'-trifluoromethylbenzyl chloride

EXAMPLE 5

N-isobutyl 11-(pentafluorobenzyloxy)-(2E,4E)-undecadienamide

In step (a), pentafluorobenzyl bromide was used instead of 3'-trifluoromethylbenzyl chloride.

EXAMPLE 6

N-isobutyl 7-benzyloxy-(2E,4E)-heptadienamide

In step (a), benzyl chloride and 1,3-propanediol were used as the main starting ingredients.

EXAMPLE 7

N-isobutyl 11-(2,4-dichlorobenzyloxy)-(2E,4E)-undecadienamide

In step (a), 2,4-dichlorobenzyl chloride was used instead of 3'trifluoromethylbenzyl chloride.

EXAMPLE 8

N-iso-butyl 10-(benzyloxy)-(2E,4E)-decadienamide

In step (a), benzyl chloride and 1,6-hexanediol were used as the main starting ingredients.

EXAMPLES 9 TO 63 AND 72 TO 116

In analogous ways the compounds of Table 1 were prepared in which Ar is a phenyl group, a is 1, n is 2, $R^4$ is hydrogen and Q is —CH$_2$—:

TABLE 1

| Ex No. | $R^6$ | b + c | $R^5$ |
|---|---|---|---|
| 9 | H | 2 | isobutyl |
| 10 | H | 4 | 1-methylpropyl |
| 11 | 3-CF$_3$ | 2 | isobutyl |
| 12 | 2,3-diCl | 5 | isobutyl |
| 13 | 3,4-methylenedioxy | 3 | isobutyl |
| 14 | 3-Br | 3 | isobutyl |
| 15 | 3,4-methylenedioxy | 3 | cyclohexyl |
| 16 | 3-Br | 3 | cyclopropylmethyl |
| 17 | 3-Br | 3 | 2-methoxypropyl |
| 18 | H | 5 | 1-methylpropyl |
| 19 | 3-CF$_3$ | 2 | 2-methoxypropyl |
| 20 | 2,3-Cl$_2$ | 5 | 2-methoxypropyl |
| 21 | 2,3-Cl$_2$ | 5 | cyclopropylmethyl |
| 22 | 3-CF$_3$ | 2 | cyclopropylmethyl |
| 23 | H | 6 | 1-methylpropyl |
| 24 | 3,4-methylenedioxy | 4 | isobutyl |
| 25 | 3,4-methylenedioxy | 5 | isobutyl |
| 26 | 3-Cl | 3 | isobutyl |
| 27 | 3-Cl | 3 | 2-methoxypropyl |
| 28 | 3-Cl | 3 | cyclopropylmethyl |
| 29 | H | 5 | isobutyl |
| 30 | H | 6 | isobutyl |
| 31 | 3,5-Cl$_2$ | 5 | 1-methylpropyl |
| 32 | 3,5-Cl$_2$ | 5 | isobutyl |
| 33 | 2,4-Cl$_2$ | 3 | isobutyl |
| 34 | 3-CN | 3 | isobutyl |
| 35 | 3-CN | 3 | 2-methylbutyl |
| 36 | 3-CN | 3 | 2-methoxypropyl |
| 37 | 3-CN | 5 | 2-methoxypropyl |
| 38 | 3-CN | 5 | isobutyl |
| 39 | 3-CN | 5 | cyclopropylmethyl |
| 40 | 3,5-Cl$_2$ | 3 | isobutyl |
| 41 | 3-F | 3 | isobutyl |
| 42 | 3-F | 5 | isobutyl |
| 43 | 3-CF$_3$ | 4 | isobutyl |
| 44 | 3-CF$_3$ | 4 | 2-methoxypropyl |
| 45 | 3-CF$_3$ | 3 | 2-methoxypropyl |
| 46 | 3-CF$_3$ | 3 | 1-methylpropyl |
| 47 | 2,5-Cl$_2$ | 3 | isobutyl |
| 48 | 3-CF$_3$ | 4 | isobutyl |
| 49 | 3,5-dimethyl | 3 | isobutyl |
| 50 | 2,6-dichloro | 3 | isobutyl |
| 51 | 3,4-dichloro | 3 | isobutyl |
| 52 | 3-CF$_3$ | 3 | 3-methylbutyl |
| 53 | 3-CF$_3$ | 3 | 2-methylpropyl-2-enyl |
| 54 | 3-CF$_3$ | 3 | 1,2-dimethylpropyl |
| 55 | 3-CF$_3$ | 3 | isopropyl |
| 56 | 3,5-(CF$_3$)$_2$ | 3 | isobutyl |
| 57 | 3,5-(CF$_3$)$_2$ | 3 | 2-methylprop-2-enyl |
| 58 | 4-tertiary butyl | 3 | isobutyl |
| 59 | 2,5-Cl$_2$ | 5 | isobutyl |
| 60 | 3,5-Cl$_2$ | 3 | 2-methylpropyl |
| 61 | 3,5-(CF$_3$)$_2$ | 3 | 2-methoxypropyl |
| 62 | 3-CF$_3$ | 3 | 2-chloropropyl |
| 63 | 3-F | 3 | 1,2-dimethylpropyl |
| 72 | 3,5-F$_2$ | 5 | isobutyl |
| 73 | 3,5-F$_2$ | 3 | isobutyl |
| 74 | 3-CF$_3$ | 3 | 2-methyl-2-hydroxypropyl |
| 75 | 3-CF$_3$ | 3 | |
| 76 | 3,4-Cl$_2$ | 5 | 1,2-dimethylpropyl |

TABLE 1-continued

| Ex No. | R⁶ | b + c | R⁵ |
|---|---|---|---|
| 77 | 2,6-Cl₂ | 5 | 1,2-dimethylpropyl |
| 78 | 3,4-Cl₂ | 5 | isobutyl |
| 79 | 2,6-Cl₂ | 5 | isobutyl |
| 80 | 3-SO₂NEt₂ | 3 | isobutyl |
| 81 | 3-SO₂NEt₂ | 5 | isobutyl |
| 82 | 3-OCH₂CF₃ | 3 | isobutyl |
| 83 | 4-OCF₃ | 3 | isobutyl |
| 84 | 3-OCH₂CF₃ | 3 | 1,2-dimethylpropyl |
| 85 | 4-OCF₃ | 3 | 1,2-dimethylpropyl |
| 86 | 3-NO₂ | 3 | isobutyl |
| 87 | 2,4-F₂ | 3 | isobutyl |
| 88 | 2,4-F₂ | 3 | 1,2-dimethylpropyl |
| 89 | 3-CF₃ | 3 | isopropyloxy |
| 90 | 3-CF₃ | 3 | 2,2-dimethylpropyl |
| 91 | 3-CF₃ | 3 | 1,1-dimethylpropyl |
| 92 | 3-CF₃ | 3 | 2,2-dimethylcyclopropyl |
| 93 | 4-Cl | 3 | isobutyl |
| 94 | 3-CF₃ | 3 | 1-ethylpropyl |
| 95 | H | 7 | isobutyl |
| 96 | H | 3 | isobutyl |
| 97 | 4-OEt | 3 | isobutyl |
| 98 | 2-Cl, 4-F | 3 | isobutyl |
| 99 | 3,5-(CF₃)₂ | 5 | 1,2-dimethylpropyl |
| 100 | 3,5-(CF₃)₂ | 5 | 1-methylpropyl |
| 101 | H | 5 | α-methylbenzyl |
| 102 | 3-OPh | 3 | 1,2-dimethylpropyl |
| 103 | 3-OPh | 3 | isobutyl |
| 104 | 2-Cl | 3 | isobutyl |
| 105 | 4-CF₃ | 3 | isobutyl |
| 106 | 4-CF₃ | 3 | 1,2-dimethylpropyl |
| 107 | 3-F | 4 | 3-methylbutyl |
| 108 | 3,5-(CF₃)₂ | 5 | 1,2,2-trimethylpropyl |
| 109 | 3,5-(CF₃)₂ | 5 | 2,2-dimethylcyclopropyl |
| 110 | 3-SEt | 3 | 1,2-dimethylpropyl |
| 111 | 3-S(O)Et | 3 | 1,2-dimethylpropyl |
| 112 | 2-F, 5-Cl | 3 | isobutyl |
| 113 | 2-,5-F | 3 | isobutyl |
| 114 | 4Ph | 5 | isobutyl |
| 115 | 3-F₂CF₃ | 3 | isobutyl |
| 116 | 3-F₂CF₃ | 3 | 1,2-dimethylpropyl |

EXAMPLES 64 TO 71

In analogous ways, the following compounds were prepared:

| Example No. | Name |
|---|---|
| 64 | N—isobutyl 8-(2-(3'-trifluoromethylbenzyloxy)-ethoxy)-octa-2E, 4E-dienamide |
| 65 | N—isobutyl 8-(1-(3-trifluoromethylphenyl)ethoxy)-octa-2E, 4E-dienamide |
| 66 | N—isobutyl 9-(2-(3',5'-dichlorophenoxy)-ethoxy)-nona-2E, 4E-dienamide |
| 67 | N—2-methoxypropyl 9-(2-thienylmethoxy)nona-2E, 4E-dienamide |
| 68 | N—isobutyl 9-(2-thienylmethoxy)nona-2E, 4E-dienamide |
| 69 | N—isobutyl 11-(2-thienylmethoxy)undeca-2E, 4E-dienamide |
| 70 | N—isobutyl 9-(2-furfurylmethoxy)nona-2E, 4E-dienamide |
| 71 | N—isobutyl 9-benzylthiooxynona-2E, 4E-dienamide |

EXAMPLES 117–132

In analogous ways the following compounds were prepared.

| | |
|---|---|
| 117 | N—Isobutyl 11-(α-ethynylbenzyloxy)undeca-2E, 4E-dienamide |
| 118 | N—Isobutyl 9-(2-naphthylmethoxy)nona-2E,4E-dienamide |
| 119 | N—Isobutyl 11-(2-furfuryloxy)undeca-2E,4E-dienamide |
| 120 | N—Isobutyl 11-(3-thienylmethoxy)undeca-2E, 4E-dienamide |
| 121 | N—Isobutyl 9-(3-thienylmethoxy)nona-2E,4E-dienamide |
| 122 | N—Isobutyl 11-(3-trifluoromethylphenyl)-10-oxo-undeca-2E,-dienamide |
| 123 | N—Isobutyl 10-benzthioxy-deca-2E,4E-dienamide |
| 124 | N—Isobutyl 9-(3-furfuryloxy)nona-2E, 4E-dienamide |
| 125 | N—Isobutyl 11-(3-furfuryloxy)undeca-2E,4E-dienamide |
| 126 | N—Isobutyl N'—methyl-N'—benzyl-9-aminoundeca-2E, 4E-dienamide |
| 127 | N—Isobutyl 8-[1-(3',5'-dichlorophenoxy)-methoxy]-octa-2E,4E-dienamide |
| 128 | N—Isobutyl 10-[1-(3',5'-dichlorophenoxy)-methoxy)-deca-2E,4E-dienamide |
| 129 | N—Isobutyl [8-(octa-2E,4E-dienamide)yl benzyl sulphoxide |
| 130 | N—1-methylpropyl 9-[2-(3',5'-dichlorophenoxy)-ethoxy)-nona-2E,4E-dienamide |
| 131 | N—Isobutyl 9-(α-methylbenzyloxy)nona-2E, 4E-dienamide |
| 132 | N—Isobutyl 9-(α-cyanobenzyloxy)nona-2E,4E-dienamide |

BIOLOGICAL ACTIVITY

A. Lethal Activity Against House Flies

The activity of compounds of the invention against female *Musca domestica* (WRL strain), with and without co-treatment with a synergist, was demonstrated by application to the test insect of a solution of the compound under test in cellosolve.

The test compound was applied with the application of the synergist (6 μg piperonyl butoxide (PB) per insect). Mortality was assessed after 48 hrs.

The results are shown below in Table 2.

TABLE 2

| Compound of Example No. | LD₅₀(μg/fly) (synergised) | LD₅₀(μg/fly) (unsynergised) |
|---|---|---|
| 1 | ≈0.6 | ≈6 |
| 2 | 0.2 | ≈6 |
| 4 | 0.025 | 0.12 |
| 8 | 5< | |
| 13 | ≈1.8 | 6< |
| 14 | 0.18 < 0.6 | 1.8 < 6 |
| 25 | 1.8 < 6 | ≈10 |
| 26 | 0.18 < 0.6 | 1.8 < 6 |
| 27 | ≈1.8 | |
| 28 | 1.8 < 6 | |
| 31 | 0.11 | ≈1.5 |
| 34 | 6< | |
| 41 | ≈0.9 | |
| 43 | ≈6 | |
| 45 | ≈1.8 | 10< |
| 47 | 0.18 < 0.6 | 1.8 < 6 |
| 49 | 3 < 5 | |
| 52 | 1.8 < 6 | |
| 53 | 0.18 < 0.6 | |
| 54 | 0.18 < 0.6 | |
| 58 | ≈1.8 | |
| 62 | ≈1.8 | |
| 64 | ≈10 | |
| 65 | 0.18 < 0.6 | ≈10 |
| 66 | 0.06 < 0.18 | 1.8 < 6 |
| 67 | 6 < 10 | |
| 70 | 6 < 10 | |
| 72 | 0.3 < 0.9 | |
| 74 | ≈5 | |
| 76 | ≈0.6 | 6 < 10 |
| 80 | ≈10 | |
| 82 | 0.6 < 1.8 | 6 < 10 |
| 83 | 0.6 < 1.8 | |
| 86 | 1.8 < 6 | |
| 88 | 0.18 < 0.6 | |
| 89 | 5< | |
| 90 | 0.3 < 0.9 | |
| 91 | 0.9 < 3 | |
| 92 | 0.3 < 0.9 | |
| 95 | ≈5 | |

TABLE 2-continued

| Compound of Example No. | LD$_{50}$(μg/fly) (synergised) | LD$_{50}$(μg/fly) (unsynergised) |
|---|---|---|
| 96 | 3 < 5 | |
| 97 | 1.8 < 6 | |
| 99 | ≈0.02 | |
| 103 | ≈0.9 | |
| 104 | ≈0.3 | |
| 105 | 0.9 < 3 | |
| 108 | 0.09 | |
| 109 | 0.09 | |
| 117 | ≈1.8 | |
| 118 | 0.9 < 3 | |
| 122 | 1.5< | |
| 123 | 6 < 10 | |
| 124 | 1.8 < 6 | |
| 126 | 20< | |
| 127 | 0.9 < 3 | |
| 130 | 0.09 < 0.3 | |

Key
≈ means "about"
1.5< means a value greater than 1.5
0.9 < 3 means a value between 0.9 and 3.0

B. Knockdown Activity Against Mosquitoes

The knockdown activity of compounds was assessed as follows: Caged female *Culex quinquefasciatus* were sprayed in a wind tunnedl with 0.2 ml of a solution of the compound in odourless petroleum distillate (OPD)-/dichloromethane (80/20) and knockdown was assessed at minute intervals for 10 mins. The insects were transferred to a holding cup and kept for 24 hrs with sugar/-water. Mortalities were assessed at 24 hrs. The results are given in Table 3.

TABLE 3

| Compound of Example No. | % cpd (with piperonyl butoxide) | kT$_{50}$ min | KD$_{10\ min}$ % effect | Kill % |
|---|---|---|---|---|
| 2 | 0.3 (1.5) | 1.2 | 100 | 71 |
|   | 0.03 (0.15) | 8.6 | 56 | 4 |
| 26 | 0.3 (1.5) | <1 | 100 | 80 |
|   | 0.03 (0.15) | 3.2 | 63 | 21 |
| 41 | 0.1 (0.5) |  | 35 |  |
| 63 | 0.1 (0.5) | 1.7 | 100 | 56 |
| 66 | 0.1 (0.5) | 1.2 | 96 | 40 |

C. Knockdown Activity Against Houseflies

Mixed sex *Musca domestica* were held in a Kearns and March chamber and sprayed with 0.2 ml of a solution of the compound in OPD/dichloromethane. Knockdown was assessed at 1 min. intervals for 10 mins. The results are given in Table 4.

| Compound of Example No. | % cpd (with piperonyl butoxide) | kT$_{50}$ min | KD$_{10\ min}$ % effect |
|---|---|---|---|
| 2 | 0.1 | 6.1 | 86 |
| 26 | 0.3 (1.5) | 2.3 | 100 |
| 41 | 0.3 (1.5) | 2.6 | 100 |
| 63 | 0.3 (1.5) | 2.3 | 100 |
| 66 | 0.1 (0.5) | 5.1 | 96 |
| 53 | 0.1 (0.5) | 3.2 | 100 |

D. Activity Against Grain Beetles

The activity of compounds of the invention against grain pests was demonstrated by the exposure of *Sitophilus granarius* in deposits of the compound under test and a synergist (piperonyl butoxide) in a 1:5 ratio on grain. Mortality was assessed after 6 days.
The results are shown below (Table 5):

| Compound of Example No. | Application rate ppm cpd (+ pb) | % mortality |
|---|---|---|
| 2 | 20 (100) | 84 |
| 4 | 50 (500) | 100 |

E. Activity Against Cockroaches

The activity of compounds of the invention against male *Blattella germanica* was demonstrated by exposure of the insect for 1 hour to a deposit of the compound under test and a synergist (piperonyl butoxide) in a 1:1 ratio on glass. Knockdown was assessed after 10 and 60 minutes and mortality after 1 day and 6 days.
The results are shown below in Table 6:

| Compound of Example No. | Application rate mg/m$^2$ (+ pb) | % mortality 1 day | % mortality 6 day |
|---|---|---|---|
| 2 | 1400 (1400) | 50 | 50 |
| 4 | 700 (700) | 32 | 32 |

F. Activity Against Mosquito Larvae

The activity of compounds of the invention against mosquito larvae was demonstrated by the exposure of third instar larvae of *Aedes aegypti* to an aqueous suspension of the compound under test and synergist (piperonyl butoxide) in a 1:5 ratio.
The results are shown below in Table 7:

TABLE 7

| Compound of Example No. | Application rate ppm cpd (+ pb) | % mortality |
|---|---|---|
| 2 | 2.5 (12.5) | 100 |

G. Activity Against the Cattle Tick (a) Injection

The compound was supplied as a 50 mg/liter solution in DMSO:Acetone (1:1). Administration of the compound was by means of a microapplicator which was preset to deliver 0.2 μl of solution. The compound in solution was injected into fully engorged female *Boophilus microplus*, susceptible strain, at a site just lateral to the mouthparts at the rate of 10 μg/tick. Reducing the concentration reduced the dose delivered.

After injection the ticks were maintained at 24° C. and 85% RH for 14 days. At this time the ticks were examined for the presence of viable eggs which gave the percent inhibition of reproduction (% IR). The number of dead ticks was also noted, and the results given in Table 8:

TABLE 8

| Compound of Example No. | Dose (μg) | No. of ticks | % IR | % kill |
|---|---|---|---|---|
| 31 | 10 | 10 | 60 | 0 |
|   | 3 | 10 | 70 | 10 |
|   | 1 | 10 | 40 | 0 |
| 54 | 10 | 10 | 100 | 20 |
|   | 3 | 10 | 90 | 30 |
|   | 1 | 10 | 40 | 10 |
| 63 | 10 | 10 | 100 | 5 |
| 85 | 10 | 10 | 100 | 50 |

(b) Immersion

The compound was supplied as a 100 mg/liter solution in Esso 200/wetters. Dilution with water gave the required concentrations. Groups of 20 fully engorged female *B. microplus* susceptible strain were placed in a mesh basket which was immersed in the test dilution for 10 minutes. After immersion the ticks were removed, dried and then fixed to double-sided adhesive tape which was itself affixed to white plastic boards. The boards holding the ticks were held at 24° C. and 85% RH for 14 days.

Individual egg masses were scored for 0-4 for quality and quantity and the total score for each group was obtained. The scores were corrected for water control oviposition, plotted on log-probit paper and the % concentration inhibiting 50% and 99% of viable oviposition determined (IR50 and IR99, respectively). Similarly, the concentrations for morality of 50% and 99% were determined.

The results are shown below in Table 9:

TABLE 9

| Compound of Example No. | IR50 | IR99 | LC50 | LC90 |
|---|---|---|---|---|
| 54 | 0.001 | 0.019 | 0.04 | >0.046 |

H. Activity Against Mustard Beetle (Phaedon cochleariae)

Second-instar larvae were used in all the tests and compounds were applied topically to the dorsal surface of the abdomen, using a microapplicator. Between 10 and 33 larvae were used at each concentration of the chemicals. Analar acetone and Analar butanone were used as solvents. In the first tests a 0.5 μl droplet was applied to each larva but after this the droplet size was increased to 1 μl as the larvae were unaffected by the solvents.

After treatment, all the larvae (usually 20) tested at a particular concentration were confined together on turnip leaves. The leaves were placed on damp filter paper in a petri dish and covered with a second layer of filter paper in the lid of the dish.

The petri dishes were maintained in an incubator at 20° C. and 16 h light. The turnip leaves were replaced as they were eaten by the larvae.

The larvae were assessed at intervals, from 1 h to 216 h after treatment. The following categories were used to classify the larvae:
i. Healthy larvae which were feeding and moved around the dish
ii. Paralysed larvae which writhed or exhibited little locomotory movement
iii. Dead larvae which exhibited no movement and were becoming flaccid

TABLE 10

| Compound of Example | Concentration (μg/ml) | Time after treatment (hours) | Healthy | Paralysed | Dead |
|---|---|---|---|---|---|
| 2 | 500 | 1 | 0 | 33 | 0 |
|  |  | 20 | 9 | 0 | 24 |
| 2 | 1000 | 1 | 0 | 33 | 0 |
|  |  | 20 | 4 | 0 | 29 |
| (solvent control) | — | 1 | 30 | 0 | 0 |
|  |  | 20 | 30 | 0 | 0 |

Formulations

1. Emulsifiable Concentrate

| | |
|---|---|
| Compound of Example 4 | 10.00 |
| Ethylan KEO | 20.00 |
| Xylene | 67.50 |
| Butylated Hydroxyanisole | 2.50 |
| | 100.00 |

2. Wettable Powder

| | |
|---|---|
| Compound of Example 4 | 25.0 |
| Attapulgite | 69.50 |
| Sodium isopropylbenzene sulphonate | 0.50 |
| Sodium salt of condensed naphthalene sulphonic acid | 2.50 |
| Butylated hydroxytoluene | 2.50 |
| | 100.00 |

3. Dust

| | |
|---|---|
| Compound of Example 4 | 0.50 |
| Butylated Hydroxyanisole | 0.10 |
| Talc | 99.40 |
| | 100.00 |

4. Bait

| | |
|---|---|
| Compound of Example 4 | 40.25 |
| Icing Sugar | 99.65 |
| Butylated hydroxytoluene | 0.10 |
| | 100.00 |

5. Lacquer

| | |
|---|---|
| Compound of Example 4 | 2.5 |
| Resin | 5.0 |
| Butylated Hydroxyanisole | 0.5 |
| High aromatic white spirit | 92.0 |
| | 100.00 |

6. Aerosol

| | |
|---|---|
| Compound of Example 4 | 0.30 |
| Butylated Hydroxyanisole | 0.10 |
| 1,1,1-Trichloroethane | 4.00 |
| Odourless Kerosene | 15.60 |
| Arcton 11/12. 50:50 mix | 80.00 |
| | 100.00 |

7. Spray

| | |
|---|---|
| Compound of Example 4 | 0.1 |
| Butylated Hydroxyanisole | 0.1 |
| Xylene | 10.0 |
| Odourless Kerosene | 89.8 |
| | 100.00 |

8. Potentiated Spray

| | |
|---|---|
| Compound of Example 4 | 0.1 |
| Permethrin | 0.1 |
| Butylated Hydroxyanisole | 0.1 |
| Xylene | 10.1 |
| Odourless Kerosene | 89.8 |
| | 100.0 |

I claim:
1. The compound 11-(3'-trifluoromethylbenzyloxy)-(2E,4E)-undecadienoic acid.

* * * * *